United States Patent [19]

Hagen et al.

[11] Patent Number: 4,667,035
[45] Date of Patent: May 19, 1987

[54] SUBSTITUTED TRIAZANONANES AND PROCESS FOR THEIR PREPARATION

[75] Inventors: Helmut Hagen, Frankenthal; Rolf-Dieter Kohler, Edingen-Neckarhausen, both of Fed. Rep. of Germany

[73] Assignee: BASF Aktiengesellschaft, Ludwigshafen, Fed. Rep. of Germany

[21] Appl. No.: 668,318

[22] Filed: Nov. 5, 1984

[30] Foreign Application Priority Data

Nov. 5, 1983 [DE] Fed. Rep. of Germany ....... 3340077

[51] Int. Cl.$^4$ .................. C07D 487/08; C07D 209/48
[52] U.S. Cl. .................................... 544/246; 548/476
[58] Field of Search .................. 544/246; 514/257

[56] References Cited

U.S. PATENT DOCUMENTS 4,447,607  5/1984  Johnson ............................. 544/246
4,544,755  10/1985  Hagen et al. ....................... 548/335

OTHER PUBLICATIONS

Houben-Weyl, vol. V/3, p. 378.
Noller, "Chemistry of Organic Compounds" W. B. Saunders, Philadelphia (1951), pp. 424, 533-544.
Collins, et al., Chemical Abstracts, vol. 101, 7277h, (1983).
McGeachin, Chemical Abstracts, vol. 65, 15374h-15375a, (1966).
Albert, et al., Chemical Abstracts, vol. 65, 18581h-18582b, (1966).
Albert, et al., Chemical Abstracts, vol. 69, 77253s, (1968).
Black, et al., Chemical Abstracts, vol. 73, 109770j, (1970).
Skuratowicz, et al., Chemical Abstracts, vol. 87, 39448y, (1977).
Larikova, Chemical Abstracts, vol. 98, No. 18, 150376q, (05/02/83).
Tetrahedron, vol. 36, pp. 2359-2386, (1980), Caluure.
Albert et al, J. Chem. Soc., (B), 1966, pp. 956-963.
Albert et al, J. Chem. Soc., (C), 1968, pp. 1944-1949.
Black et al, Aust. J. Chem., 1970, vol. 23, pp. 2055-2065.
Albert, Heterocyclic Chemistry, Second Edition, 1968, pp. 165-167.
Kirk-Othmer, Encyclopedia of Chemical Technology, Third Edition, vol. 3, 1978, p. 742.
Kirk-Othmer, Encyclopedia of Chemical Technology, Third Edition, vol. 19, pp. 543, 544, 548, 550, 551, 553.

*Primary Examiner*—Donald G. Daus
*Assistant Examiner*—Diana G. Rivers
*Attorney, Agent, or Firm*—Oblon, Fisher, Spivak, McClelland & Maier

[57] ABSTRACT

The novel compounds of the general formula I

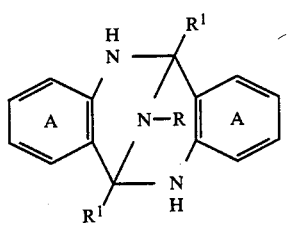

where R and $R^1$ are substituents and the rings A can be substituted and/or can carry fused rings, are useful intermediates for the preparation of, for example, dyes and active ingredients.

5 Claims, No Drawings

SUBSTITUTED TRIAZANONANES AND PROCESS FOR THEIR PREPARATION

The present invention relates to compounds of the general formula I

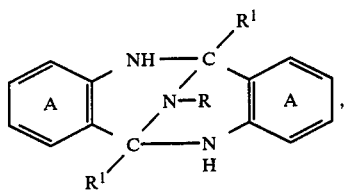

where R and $R^1$ are substituents, and the rings A can be substituted and/or can carry fused rings.

The invention relates in particular to compounds of the formula I in which R is hydrogen, unsubstituted or substituted alkyl, alkenyl or cycloalkyl, $R^1$ is hydrogen or $C_1$—$C_6$—alkyl, and the rings A can be further substituted by fluorine, chlorine or bromime or can carry fused rings.

The alkyl radicals R can have, for example, 1 to 12 carbon atoms, and can be substituted by hydroxyl, alkoxy, cyano, amino, alkylamino, dialkylamino, alkylmercapto or aryl.

Specific examples of substituted alkyl radicals R are hydroxyethyl, hydroxypropyl, methoxyethyl, ethoxyethyl, butoxyethyl, methoxypropyl, cyanoethyl, aminoethyl, dimethylaminoethyl and methylmercaptoethyl.

Alkenyl radicals R preferably have 3 to 10 carbon atoms, and cycloalkyl radicals have 5, 6 or 7 ring members, which can be substituted by hydroxyl.

Specific examples of radicals are $CH_2$—$CH=CH$—$CH_2OH$, $$CH_2-\underset{\underset{CH_3}{|}}{C}=CH-CH_2OH,$$

hydroxycyclopentyl and hydroxycyclohexyl.

$R^1$ is, for example, hexyl, pentyl, butyl, propyl, ethyl or, preferably, methyl, and in particular hydrogen.

The rings A can be substituted by, for example, fluorine, chlorine or bromine and may furthermore carry one or more unsubstituted or substituted fused rings, suitable substituents being those stated above.

To prepare the compounds of the formula I in which R' is hydrogen, a compound of the formula II

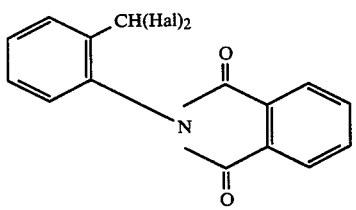

is reacted with an amine of the formula III

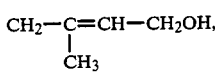

in the presence or absence of a solvent. In this formula, Hal is chlorine or bromine.

Examples of suitable solvents are chlorohydrocarbons, alcohols, glycols, glycol ethers, amides, ethers and ketones.

Specific examples of solvents are methylene chloride, chloroform, methanol, ethanol, propanol, isopropanol, ethylene glycol, methylglycol, formamide, dimethylformamide, ethylene glycol dimethyl ether and acetone.

The Examples which follow illustrate the reaction procedure. Parts and percentages are by weight, unless stated otherwise.

The compounds of the formula II can be prepared by halogenating a compound of the formula

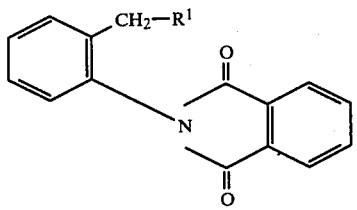

by a conventional method, R' being hydrogen

The compounds of the formula I are blocked 2-aminobenzaldehydes which can be liberated by means of an acid or base and thus made available for further reactions. The compounds of the formula I can therefore be regarded as a stable form of the 2-aminobenzaldehydes, which as a rule are unstable.

2-Aminobenzaldehydes are useful intermediates for the preparation of dye precursors, active ingredients and heterocyclic compounds (cf. for example Tetrahedron 36 (1980), 2359).

Particularly important compounds of the formula I are those in which R is hydroxyethyl, $R^1$ is hydrogen, and the rings A are unsubstituted or substituted by chlorine.

EXAMPLE 1

N-(Hydroxyethyl)-dibenzo[c,g]-2,6,9-triazabicyclo[3.3.1]-nonane 612 g of 2-dichloromethyl-N-phenylphthalimide were introduced a little at a time into 1,200 g of ethanolamine, while stirring. During this procedure, the temperature increased to 80° C. After 2 hours, 3,000 g of ice water were added, and the precipitate was filtered off under suction, washed neutral with water and dried under reduced pressure to give 255 g (96% of theory) of a colorless product of melting point 196° C.

EXAMPLE 2

N-(Hydroxyethyl)-bis(2-chlorobenzo)-[c,g]-2,6,9-triazabicyclo[3.3.1]nonane 68 g of 3-chloro-2-dichloromethyl-N-phenylphthalimide were added to 150 g of ethanolamine at 70° C., while stirring. After 1 hour, the mixture was cooled to 20° C., and 400 g of ice water were then added dropwise. The precipitate was filtered off under suction, washed with water and dried under reduced pressure to give 28 g (84% of theory) of a product of melting point 176° C.

EXAMPLE 3

N-(Aminoethyl)-dibenzo[c,g]-2,6,9-triazabicyclo[3.3.1-]nonane 20 g of 2-dichloromethyl-N-phenylphthalimide were added a little at a time to 40 g of 1,2-diaminoethane at 40° C., while stirring. After 2 hours, 150 g of ice water were added dropwise at 20° C., and the precipitate was filtered off under suction, washed neutral with water and dried under reduced pressure to give 8 g (88% of theory) of a colorless product of melting point 182° C.

Compounds of the formula

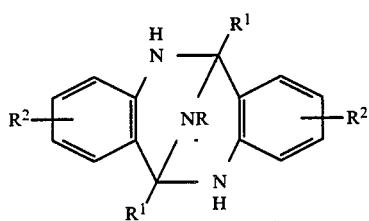

can be prepared similarly to Example 1.

| Example | R | $R^1$ | $R^2$ |
|---|---|---|---|
| 4 | CH₂CH₂OH | H | 3-Cl |
| 5 | CH₂CH₂OH | H | 4-Cl |
| 6 | CH₂CH₂OH | H | 5-Cl |
| 7 | CH₂CH₂OH | H | 2-Br |
| 8 | CH₂CH₂OH | H | 3-Br |
| 9 | CH₂CH₂OH | H | 4-Br |
| 10 | CH₂CH₂OH | H | 5-Br |
| 11 | CH₂CH₂OH | CH₃ | H |
| 12 | CH₂CH₂NH₂ | H | 2-Cl |
| 13 | CH₂CH₂N(CH₃)₂ | H | H |
| 14 | CH₂CH₂N(CH₃)₂ | H | 2-Cl |
| 15 | CH₂—CH(OH)—CH₃ | H | H |
| 16 | CH₂—CH(OH)—CH₃ | H | 2-Cl |
| 17 | CH₂—C(OH)—CH₃ | H | H |

We claim:

1. A compound of the formula:

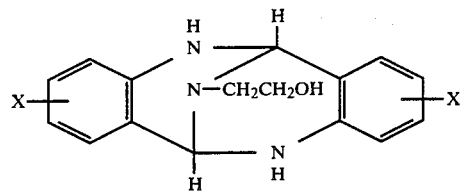

wherein X is hydrogen or chlorine.

2. Process for the production of compounds of the formula:

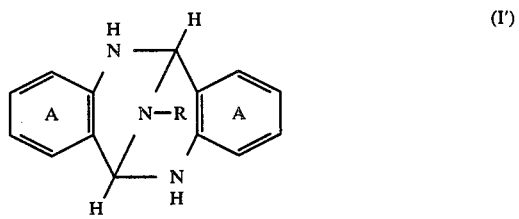

(I')

wherein R is a substituent and the rings A may be substituted, which process comprises reacting a compound of the formula:

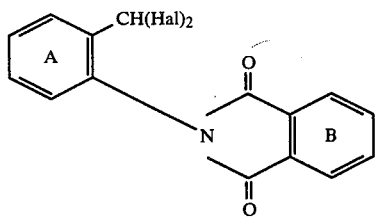

wherein Hal is chlorine or bromine and the ring B may be substituted, with an amine of the formula R NH₂ (III) optionally in the presence of a solvent.

3. Process according to claim 2, wherein ring A in the formula is unsubstituted or substituted by fluorine, chlorine or bromine, and R is hydrogen, optionally substituted alkyl, alkenyl, hydroxyalkenyl, cycloalkyl or hydroxycycloalkyl.

4. Process according to claim 3 wherein R is hydrogen, alkyl, alkyl substituted by hydroxyl, alkoxy, cyano, amino, alkylamino, dialkylamino, or alkylmercapto, alkenyl, hydroxyalkenyl, cycloalkyl or hydroxycycloalkyl, in which the alkyl radicals can have 1 to 12 carbon atoms, the alkenyl radicals 3 to 10 carbon atoms and the cycloalkyl radicals have 5, 6 or 7 ring members.

5. Process according to claim 4 in which 2-dichloromethyl-N-phenylphthalimide is reacted with ethanolamine at a temperature and for a time to produce N-(hydroxyethyl)-dibenzo[c.g.]-2,6,9-triazobicyclo[3.3.1]-nonane.

* * * * *